United States Patent [19]

Barker

[11] Plant 4,628

[45] Jan. 20, 1981

[54] POTENTILLA

[75] Inventor: David A. Barker, Much Hadham, England

[73] Assignee: Monrovia Nursery Company, Azusa, Calif.

[21] Appl. No.: 27,233

[22] Filed: Apr. 5, 1979

[51] Int. Cl.[3] ..... A01H 5/00

[52] U.S. Cl. ..... Plt./54

[58] Field of Search ..... Plt./54

*Primary Examiner*—Robert E. Bagwill

*Attorney, Agent, or Firm*—Edmond F. Shanahan

[57] ABSTRACT

An ornamental, flowering shrub of the genus *Potentilla fruticosa,* having as its more important novel characteristic the ability to produce flowers which vary from pink to red in color, a color not heretofore known in this genus. (RHS Color Chart Red Group 53C to 48C). Fading occurs as in related Potentillas, but to a pale pink color, but this is believed to be reduced by partial shade and increased by very wet or very hot, dry conditions. The plant is more dwarf than its parent. Present size of parent plant is 40 cm. high, 85 cm. maximum diameter (at age of 3½ years).

2 Drawing Figures

DESCRIPTION

This invention relates to a new variety of *Potentilla fruticosa* with pink to red flowers and typical foliage. The plant, a chance seedling of *Potentilla fruticosa* Red Ace (U.S. Plant Pat. No. 4,226) was raised by Dr. D. A. Barker in 1975 at his home at Hopleys, Much Hadham, Hertfordshire, England, where he discovered Red Ace. The new variety first flowered in 1976. The plant has been reproduced asexually by means of cuttings achieving first quality, consistent with true plants bearing all the characteristics of the parent plant. No seedlings have yet been obtained.

The accompanying drawing comprises two color photographs of a plant typical of the novel Pink Potentilla. The upper photograph contains a scale showing dimensions. Both photographs show the range of pink and red coloring of the flowers.

The plant is a seedling of *Potentilla fruticosa* Red Ace; the pollen parent is unknown. The plant flowers from mid-June to mid-October.

Like other Potentillas, the new plant requires a temperate, rather than a dry warm climate; and like other Potentillas, the leaves are alternate pinnate or palmate, and the flowers have the characteristic bracted calyx, five petals, and a fruit consisting of many small achenes heaped on a dry receptacle.

Throughout the following specification, colors are specified by reference to the Royal Horticultural Society Colour Chart.

BUD

The buds are indistinguishable, before flowering, from the yellow buds of the probable seedling parents. Before the calyx breaks, the bud is typical of Potentillas in size and structure, but the outer surfaces of the yellow petals have an occasional rose red streak. The inner surfaces of the petals are uniformly rose red, under suitable climatic conditions.

BLOOM

The outstanding novelty of the new plant is the rose red coloring of the flowers, easily distinguished from its parent, Red Ace, by the lack of orange in the hue. Typically the newly opened flower appears with petals of R.H.S. Color Chart Red Group 53C.

When the flower is fully opened, its typical size is about one inch. Its five petals have an upper surface color varying from R.H.S. Color Chart Red Group 53C to 48C. However, there is sometimes a considerable variation in the colors of the flowers on the same plant and under ideal conditions some flowers are an intense rich red shade which cannot be matched on the R.H.S. Color Chart.

The petals have an undersurface color of R. H. S. Color Chart Yellow Group 13D.

Extra petals occasionally occur, sometimes curled at the edges.

The flowers grow through many summer and fall color stages depending on the weather. In continual heat and drought, the red colors above mentioned fade, in uneven patches, to pale pinks in the range R.H.S. 49C and R.H.S. 49D, to produce a mottled pink and red coloring. The petals return to their original colors on cooler and moister conditions. Fading also occurs with excessive rain. Fading is least in the fall when the night temperatures are cool and flowering is most prolific. Present observations suggest that color maintenance is best in partial shade conditions.

FOLIAGE

The foliage resembles that of Potentillas generally, except that leaf color is somewhat distinctive: Upper side color is usually R.H.S. Color Chart Yellow Green Group 146B; underside color is generally R.H.S. Color Chart Green Group 138D.

The indumentum bears some slightly grey hairs. The leaf structure is typical of Potentillas generally.

GROWTH

The shrub exhibits a low-growing compact habit with spreading branches and is considerably more dwarf and a little less vigorous than its parent Potentilla, U.S. Plant Pat. No. 4,226.

The present growth indicates a probable mature height of 1¼ to 1½ feet and a spread of 3 feet. The growth is dense and the plant makes an excellent ground cover.

I claim:

1. A new and distinct variety of *Potentilla fruticosa* substantially as described herein and capable of producing flowers having a range of colors of red to pink, distinct from previously known Potentillas.

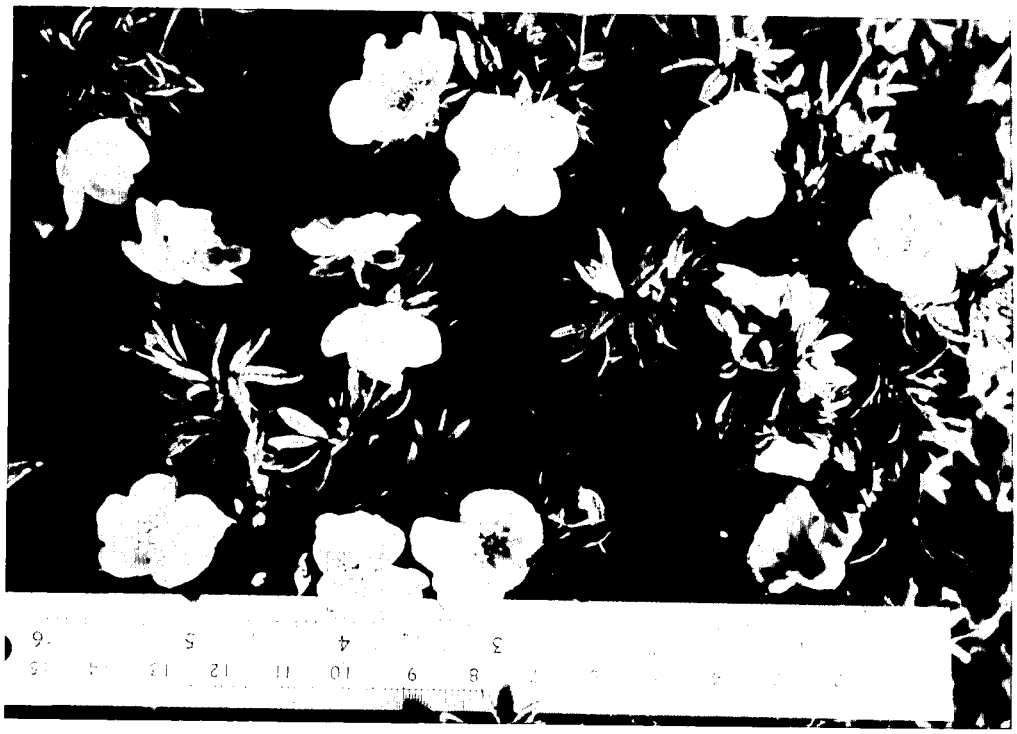
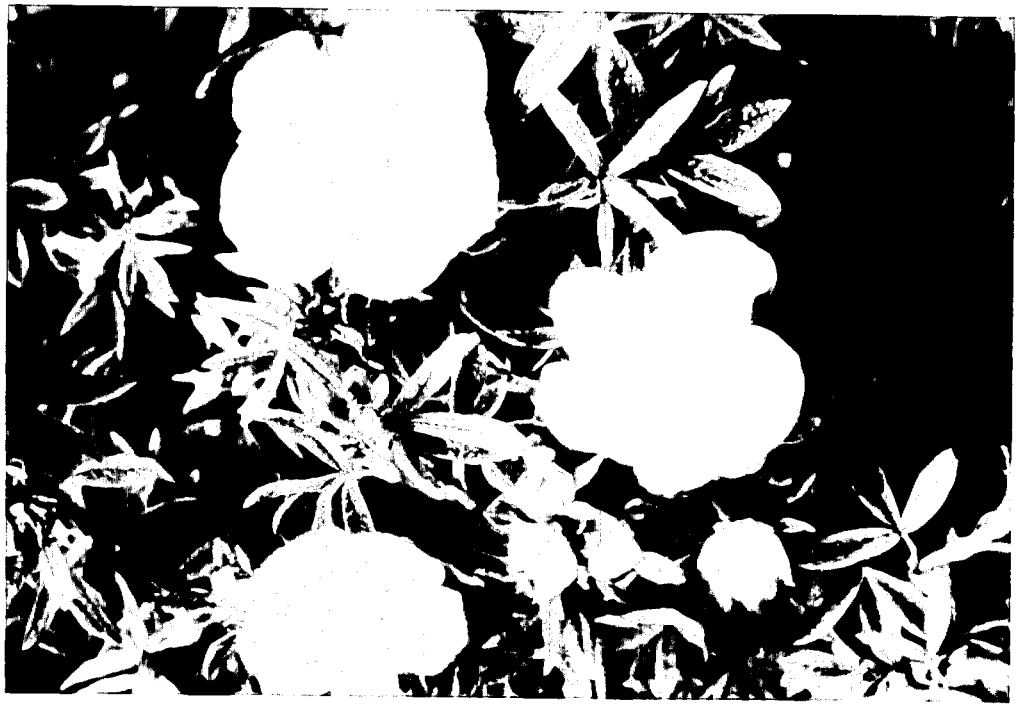

* * * * *